United States Patent [19]
Villareal

[11] Patent Number: 6,092,273
[45] Date of Patent: Jul. 25, 2000

[54] METHOD AND APPARATUS FOR A STENT CRIMPING DEVICE

[75] Inventor: Plaridel K. Villareal, San Jose, Calif.

[73] Assignee: Advanced Cardiovascular Systems, Inc., Santa Clara, Calif.

[21] Appl. No.: 09/123,844

[22] Filed: Jul. 28, 1998

[51] Int. Cl.[7] ................................................... B21D 39/00
[52] U.S. Cl. ............................ 29/516; 29/282; 29/515; 606/1; 606/108
[58] Field of Search .................................... 29/282, 283.5, 29/515, 516, 517, 715; 606/1, 108, 198; 623/1

[56] References Cited

U.S. PATENT DOCUMENTS

| | | |
|---|---|---|
| 696,289 | 3/1902 | Williams . |
| 4,468,224 | 8/1984 | Enzmann et al. . |
| 4,546,646 | 10/1985 | Williams et al. . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |

(List continued on next page.)

FOREIGN PATENT DOCUMENTS

| | | |
|---|---|---|
| 159065 | 2/1921 | United Kingdom . |
| WO 98/14120 | 4/1998 | WIPO . |
| WO 98/19633 | 5/1998 | WIPO . |

OTHER PUBLICATIONS

U.S. Patent Application Serial No. 09/063,905 filed Apr. 21, 1998.
U.S. Patent Application Serial No. 09/063,587 filed Apr. 21, 1998.
U.S. Patent Application Serial No. 09/069,010 filed Apr. 28, 1998.
U.S. Patent Application Serial No. 09/069,011 filed Apr. 28, 1998.
U.S. Patent Application Serial No. 09/072,925 filed May 5, 1998.
U.S. Patent Application Serial No. 09/169,270 filed Oct. 9, 1998.
*The eXTraordinary Stent*, C.R. Bard Brochure (Undated).
U.S. Patent Application Serial No. 08/795,335 filed Feb. 4, 1997.
U.S. Patent Application Serial No. 08/837,771 filed Apr. 22, 1997.
U.S. Patent Application Serial No. 08/893,936 filed Jul. 15, 1997.
U.S. Patent Application Serial No. 08/962,632 filed Nov. 3, 1997.
U.S. Patent Application Serial No. 09/024,910 filed Feb. 17, 1998.
U.S. Patent Application Serial No. 09/030,261 filed Feb. 25, 1998.

*Primary Examiner*—David P. Bryant
*Assistant Examiner*—Essama Omgba
*Attorney, Agent, or Firm*—Fulwider Patton Lee & Utecht, LLP

[57] ABSTRACT

A stent crimping tool for firmly and uniformly crimping a stent onto a balloon catheter is constructed from a stationary plate and a sliding platform connected to the stationary plate and slidable linearly relative thereto. A closing plate is hinged to the sliding platform so that it at least partially overlies the stationary plate in a down position, and swings away from the stationary plate to an up position, whereby the stent already having been hand crimped onto the balloon catheter is placed on the stationary plate from a lateral position, and the closing plate is moved to the down position to hold the stent between the closing plate and the stationary plate so that an external force on the closing plate as well as translational motion of the closing plate together crimp the stent onto the balloon catheter. The surfaces engaging the stent may be covered by elastomeric pads having ridges corresponding in location to respective rings or cylindrical elements of the stent.

20 Claims, 2 Drawing Sheets

U.S. PATENT DOCUMENTS

| | | |
|---|---|---|
| 4,901,707 | 2/1990 | Schiff . |
| 4,907,336 | 3/1990 | Gianturco . |
| 5,189,786 | 3/1993 | Ishikawa et al. . |
| 5,437,083 | 8/1995 | Williams et al. . |
| 5,626,604 | 5/1997 | Cottone, Jr. . |
| 5,653,691 | 8/1997 | Rupp et al. . |
| 5,672,169 | 9/1997 | Verbeek . |
| 5,693,066 | 12/1997 | Rupp et al. ............................ 606/198 |
| 5,738,674 | 4/1998 | Williams et al. . |
| 5,746,764 | 5/1998 | Green et al. . |
| 5,782,855 | 7/1998 | Lau et al. ............................... 606/194 |
| 5,782,903 | 7/1998 | Wiktor ..................................... 623/1 |
| 5,783,227 | 7/1998 | Dunham . |
| 5,785,715 | 7/1998 | Schatz . |
| 5,810,838 | 9/1998 | Solar ....................................... 606/108 |
| 5,810,871 | 9/1998 | Tuckey et al. .......................... 606/198 |
| 5,836,952 | 11/1998 | Davis et al. . |
| 5,893,867 | 4/1999 | Bagaoisan et al. .................... 606/198 |
| 5,920,975 | 7/1999 | Morales ................................... 29/282 |
| 5,931,851 | 8/1999 | Morales ................................... 606/194 |
| 5,944,735 | 8/1999 | Green et al. ........................... 606/194 |
| 5,947,993 | 9/1999 | Morales ................................... 606/198 |
| 5,948,191 | 9/1999 | Solovay .................................... 156/86 |
| 5,951,569 | 9/1999 | Tuckey et al. .......................... 606/108 |
| 6,024,737 | 2/2000 | Morales ................................... 606/1 |

METHOD AND APPARATUS FOR A STENT CRIMPING DEVICE

BACKGROUND OF THE INVENTION

The present invention relates to a method and apparatus for loading a tubular graft, such as a stent, onto the distal end of a catheter assembly of the kind used, for example, in percutaneous transluminal coronary angioplasty (PTCA) or percutaneous transluminal angioplasty (PTA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and probably through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform crimps. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error, which is antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, U.S. Pat. Nos. 5,437,083 and 5,546,646 to Williams et al.

Yet another stent crimping tool is known in the art as the BARD XT, which is actually a stent loader. It is constructed from a rigid, tubular body with a ball at one end connected to a plurality of long, thin strips passing through the tubular body. An uncrimped stent is placed over the plurality of long, thin strips, which hold the stent in an expanded state. The balloon portion of a catheter is inserted into the cylindrical space formed by the plurality of strips. When the user pulls the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, some suffer from problems such as non-uniform crimping forces, resulting in non-uniform crimps. Consequently, there is a need for improved stent crimping tools for use by physicians in a cath lab who desire to consistently crimp stents onto balloon catheters.

SUMMARY OF THE INVENTION

Both PTCA and PTA procedures have become commonplace in treating stenoses or lesions in blood vessels and coronary arteries. In approximately 35 to 40 percent of the procedures, restenosis may develop requiring a further angioplasty, atherectomy or bypass procedure to return the patency of the vessel. Intravascular stents are now being deployed after PTCA and PTA procedures, and after atherectomies, in order to help prevent the development of restenosis. Importantly, such stents, mounted on the balloon portion of a catheter, must be tightly crimped to provide a low profile delivery diameter, and to make certain that the stent stays on the balloon until the balloon is expanded and the stent is implanted in the vessel.

The present invention is directed to a crimping tool that can repeatedly provide a uniform and tight crimp to ensure the low profile diameter of the stent on the balloon portion of the catheter, and to ensure that the stent remains firmly attached until it is implanted in the vessel by expanding the balloon. Specifically, the present invention is directed to a stent crimping tool for crimping a stent onto a balloon catheter. In a preferred embodiment, the stent crimping tool comprises a stationary plate, a sliding platform connected to the stationary plate which is slidable linearly relative thereto, a closing plate that is hinged to the sliding platform so that the closing plate at least partially overlies the stationary plate in a down position, and swings away from the stationary plate to an up position, whereby the stent having been loaded onto the balloon catheter is placed on the stationary plate from a lateral position, and the closing plate is moved to the down position to hold the stent between the closing plate and the stationary plate so that an external force on the closing plate and translational motion of the closing plate crimp the stent onto the balloon catheter. In this manner, the pinching pressure of the stationary plate against the closing plate generates a radially inward force on the stent; the translational motion of the sliding platform effectively rolls the stent-catheter assembly to evenly distribute the crimping force for a homogeneous crimp.

In an exemplary embodiment, the closing plate and the stationary plate have facing surfaces that include contoured pads that help grip the stent. Furthermore, the pads have optional ridges, channels, or other contours that correspond with specific locations on the stent. So for example in an ACS Multi-Link™ stent, ridges in the pads can be situated to coincide with the locations of the proximal and distal rings of the stent. A ridge may be provided on the pads to grip a mid-length ring as well. These pinch points help insure uniform reduction in the diameter of the stent during the crimping procedure. The pinch or grip points also help stabilize the stent-catheter assembly during the crimping operation. Of course, the number, location, and shape of each grip point can be varied as needed.

In a preferred embodiment, a spacer having a cylindrical shape is positioned on the stationary plate to set a predetermined gap between the stationary plate and the closing plate in the down position. That gap therefore corresponds with the diameter of the spacer. Such spacers work as gap controllers to obtain repeatable and consistent diameters on the crimped stents. Furthermore, the spacers prevent overcrimping, which may potentially produce pin holes in the balloon catheter.

In alternative embodiments, a mandrel can be inserted into the balloon catheter to provide some level of internal support during the crimping process. Moreover, it is recommended that the surface directly in contact with the stent during the crimping procedure be slightly softer than the material used on the stent to allow for yield. Elastomer type materials with higher durometers may be considered.

When the stent is inserted into the stationary plate from a lateral position, a stop or riser formed into the stationary plate maintains proper alignment of the stent-catheter assembly relative to the crimping tool. The stent abuts against the stop so that the stent-catheter assembly is not inserted too far or not far enough into the tool.

Accordingly, the present invention is very simple to operate. With few moving parts and use of a spacer to set the gap between the stationary plate and closing plate, it is possible to consistently and repeatably crimp stents onto balloon catheters. Loading and unloading the stent-catheter assembly into and out of the present invention crimping tool is quick because the closing plate swings out of the way.

The present invention crimping tool is highly useful to cardiologists, for example. Such physicians are often concerned with proper deployment of the stent within the patient that it is desirable to have a consistently and reliably crimped stent. The present invention tool is further a time saver, because the stent crimping procedure can be performed fairly efficiently and quickly. These and other advantages of the present invention will become apparent from the following detailed description thereof when taken in conjunction with the accompanying exemplary drawings.

DETAILED DESCRIPTION OF THE PREFERRED EMBODIMENTS

Figure 1:
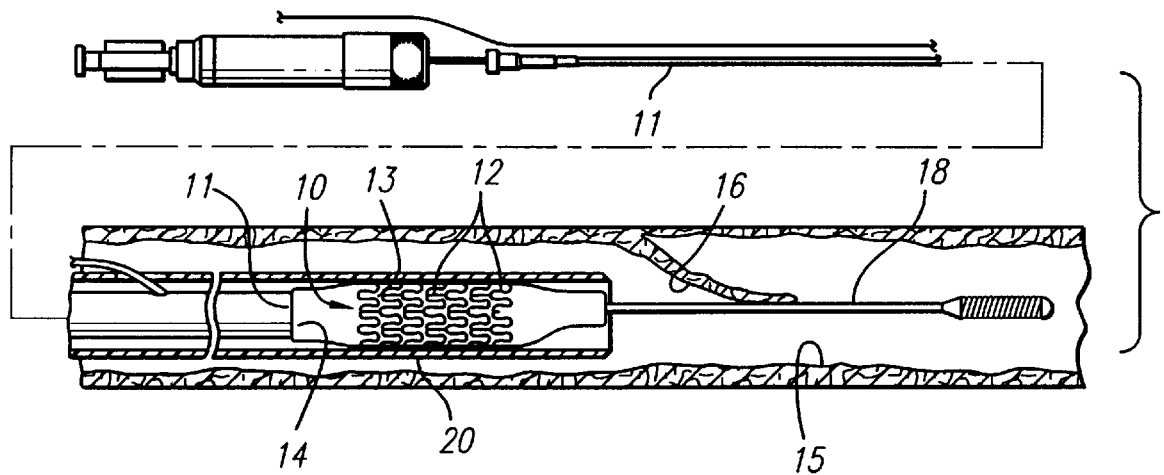
FIG. 1 is a side elevational view, partially in section, depicting a stent that has been crimped onto a balloon portion of a delivery catheter and disposed within a vessel.

FIG. 1 illustrates intravascular stent 10 which is mounted onto delivery catheter 11. Stent 10 generally comprises a plurality of radially expandable rings or cylindrical elements 12 disposed coaxially and interconnected by members 13 disposed between adjacent cylindrical elements 12. Delivery catheter 11 has an expandable portion or balloon 14 for expanding stent 10 within coronary artery 15 or other vessel such as saphenous veins, carotid arteries, arteries, and veins. Artery 15, as shown in FIG. 1, has dissected lining 16 which has occluded a portion of the arterial passageway.

Delivery catheter 11 onto which stent 10 is mounted is essentially the same as a conventional balloon dilatation catheter for angioplasty procedures. Balloon 14 may be formed of suitable materials such as polyethylene, polyvinyl chloride, polyethylene terephthalate and other like polymers. In order for stent 10 to remain in place on balloon 14 during delivery to the site of the damage within artery 15, stent 10 is compressed onto balloon 14.

An optional retractable protective delivery sleeve 20 may be provided to further ensure that stent 10 stays in place on balloon 14 of delivery catheter 11 and to prevent abrasion of the body lumen by the open surface of stent 10 during delivery to the desired arterial location. Other means for securing stent 10 onto balloon 14 may also be used, such as providing collars or ridges on the ends of the working portion, i.e., the cylindrical portion of balloon 14.

In order to implant stent 10, it is first mounted onto inflation balloon 14 on the distal extremity of delivery catheter 11. In this mounting step, stent 10 is crimped down onto balloon 14 to create a low profile. The present invention addresses this crimping procedure.

The stent-catheter assembly can be introduced into the patient's vasculature through processes known in the art. Briefly, guide wire 18 is disposed across the arterial section where an angioplasty or atherectomy has been performed requiring a follow-up stenting procedure. In some cases, the arterial wall lining may be detached so that guide wire 18 is advanced past detached or dissected lining 16 and the stent-catheter assembly is advanced over guide wire 18 within artery 15 until stent 10 is directly under detached lining 16. Prior to inflation of balloon 14, delivery sleeve 20 is retracted to expose stent 10. Depending on the balloon and stent assembly, a delivery sleeve may be unnecessary. Balloon 14 of delivery catheter 11 is then inflated using an inflation fluid. Expansion of balloon 14 in turn expands stent 10 against artery 15. Next, balloon 14 is deflated and catheter 11 is withdrawn leaving stent 10 to support the damaged arterial section. As mentioned above, in order to ensure proper seating of stent 10 on balloon 14, and to ensure proper deployment of stent 10 at the site of the damage within artery 15, the stent crimping procedure is important.

The present invention is directed to a stent crimping tool that crimps a stent onto a balloon catheter. This is preferably accomplished through tangential forces exerted by the tool on the outside surface of the stent to slowly reduce its diameter. The diameter of the stent is continuously reduced until it is stabilized on the balloon catheter.

Figure 2:
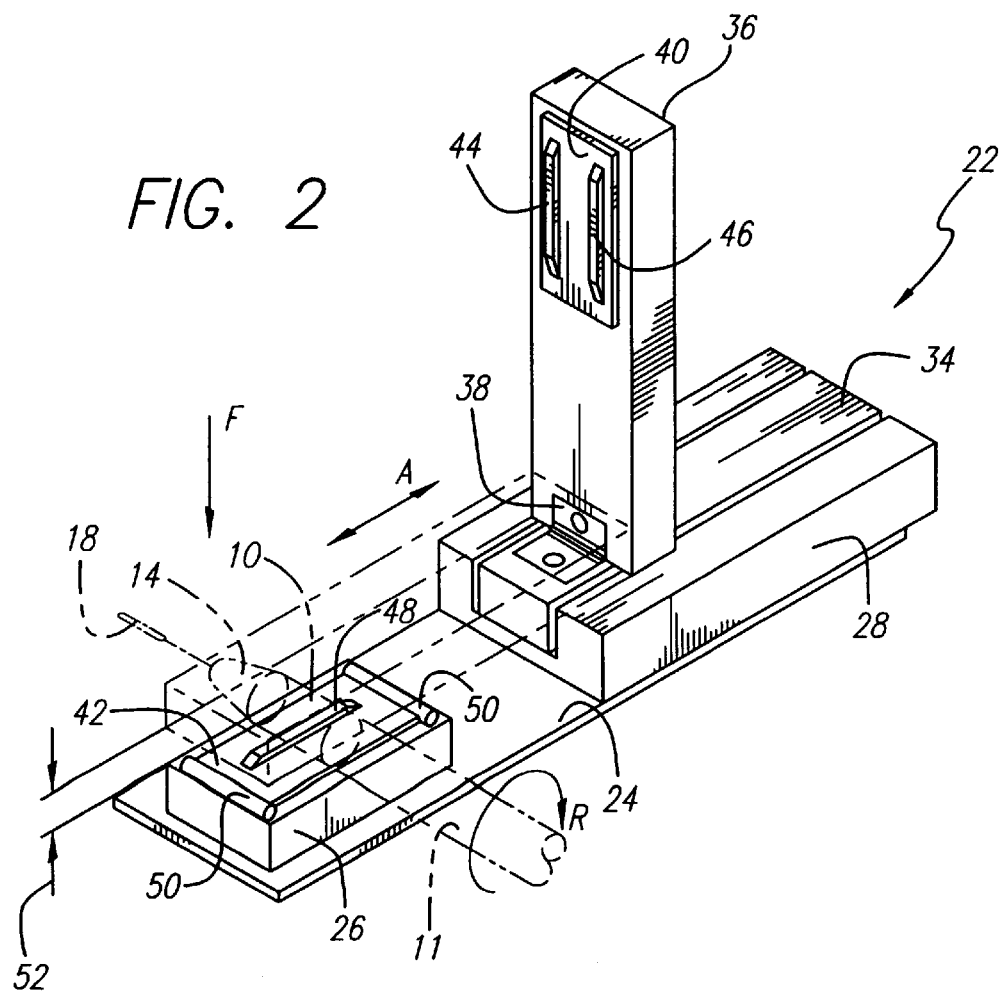
FIG. 2 is a perspective view of a preferred embodiment of the present invention showing a stent crimping tool wherein the closing plate is in an up position and the stent-catheter assembly is shown in dashed lines.

FIG. 2 provides a perspective view of a preferred embodiment of the present invention stent crimping tool 22. Stent crimping tool 22 is comprised of base plate 24 to which is mounted stationary plate 26 at one end and platform 28 at an opposite end. In the preferred embodiment shown, stationary plate 26 and platform 28 are spaced apart from each other. They are formed from or firmly mounted to base plate 24 with adhesives or fasteners to prevent relative motion therebetween.

Figure 5:
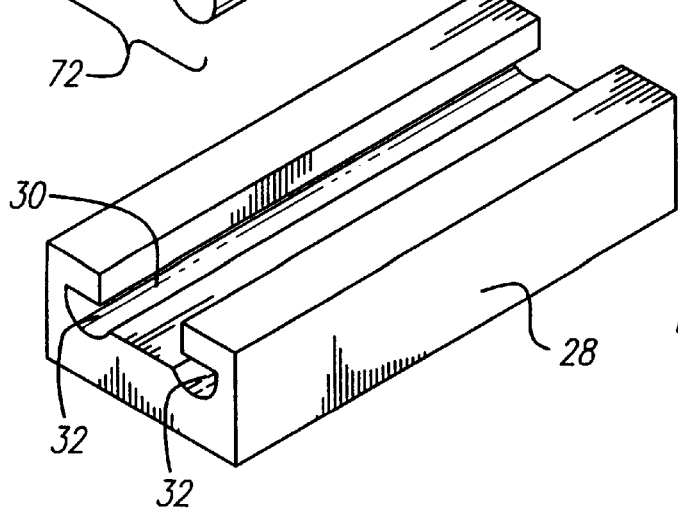
FIG. 5 is a perspective view of a preferred embodiment platform showing a channel designed to receive the dove tail of the slide shown in FIG. 4.

FIG. 5 provides a perspective view of platform 28 isolated from the other parts of stent crimping tool 22. As seen in FIG. 5, platform 28 preferably includes a channel 30 formed along a length thereof having twin parallel grooves 32 at the base of channel 30.

Figure 4:
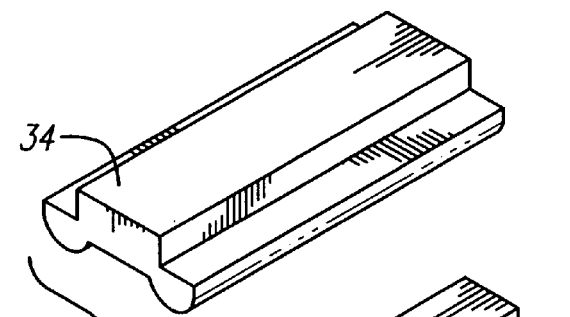
FIG. 4 is a perspective view of a slide having a dove tail to which a closing plate is attached.

Slide 34 is shown both in FIG. 2 and in isolation in the perspective view of FIG. 4. Slide 34 includes dove tail 72 that is designed to slidably engage grooves 32 and to slidably move within channel 30 of platform 28 in FIG. 5. With preferably tight tolerances in the parts, it is possible to have very precise linear movement of slide 34 within channel 30 of platform 28 with very little lateral play or slop. This minimizes the chance for inconsistent crimps due to unwanted play in the component parts of crimping tool 22.

Closing plate 36 is preferably attached to the top of slide 34 by use of hinge 38, as best seen in FIG. 2. Hinge 38 permits closing plate 36 to swing about two positions; namely, the up position as shown in solid lines, or the down position as shown in dashed lines. Hinge 38 may be loaded with an optional torsion spring, for example, to bias closing plate 36 toward the up position or the down position as needed.

In an alternative embodiment (not shown), the hinge can be made of a bar of spring steel attached at opposite ends to the slide and the closing plate. When the closing plate swings open or closed, it does so by flexing the bar. Thus, the spring steel bar can be made to resist or to forward bias the closing plate toward either the up or the down positions. The bar may, of course, be made from any resilient material known in the art.

Returning to FIG. 2, when closing plate 36 is in the down position, the underside of closing plate 36 faces the top side of stationary plate 26. These opposing surfaces are covered with optional pads 40 and 42. Pad 40 includes two raised ridges 44, 46 while pad 42 has a single ridge 48. Ridges 44, 46, 48 are preferably aligned along the longitudinal direction as indicated by arrow A. Arrow A also indicates the direction of translation of slide 34 relative to platform 28 and stationary plate 26, thereby moving closing plate 36 in its down position to an overlying alignment above stationary plate 26.

Ridges 44, 46, 48 are intended to engage the rings or cylindrical elements 12 of stent 10. Indeed, stent 10, after being optionally hand crimped to balloon 14, is inserted laterally in a direction generally perpendicular to the direction indicated by arrow A into crimping tool 22. Ideally, each ridge 44, 46, 48 engages a corresponding cylindrical element 12 of stent 10. For example, ridges 44, 46, 48 can be situated to specifically engage the distal, proximal, and middle cylindrical elements 12 of stent 10. To be sure, it has been observed that engagement of the ridges 44, 46, 48 against cylindrical elements 12 of stent 10 helps grip the stent 10 during the crimping process.

In order to control the amount of crimp on stent 10, optional cylindrical spacers 50 are positioned as shown on stationary plate 26 in FIG. 2. The diameter of each spacer 50 controls the distance of gap 52, which defines the distance between the opposing pads 40, 42 of stationary plate 26 and closing plate 36, respectively. Controlling gap 52 thus controls the amount of crimp received by stent 10. Also, use of spacers 50 to define the size of gap 52 improves the chances for a precise and repeatable crimp.

Force vector F in the general direction as shown in FIG. 2 is applied to closing plate 36 while it is in the down position. While force F is applied, closing plate 36 and slide 34 translate linearly and reciprocate along direction A to perform the crimping process.

Based on the foregoing, it is clear that a theory of operation of the present invention crimping tool 22 is essentially two plates 26, 36 sliding against one another. One of the plates 26 can be stationary while the other plate 36 is mounted on a sliding mechanism. The pinching action due to force F reduces the diameter of stent 10 while the sliding motion rolls the stent-catheter assembly as represented by arrow R to distribute the forces.

As mentioned earlier, use of optional spacers 50 controls the size of gap 52. In an alternative embodiment, a mandrel (not shown) can be inserted into delivery catheter 11 to provide a level of internal resistance in the radial direction to prevent over-crimping of stent 10 onto balloon 14. Furthermore, use of an optional mandrel positioned within the balloon 14 of catheter 11 during the crimping process ensures repeatability and a precise crimp of stent 10.

To use the present invention stent crimping tool 22, the cardiologist lays a slightly hand-crimped stent-catheter assembly onto pad 42 as represented by the dashed lines of FIG. 2. Closing plate 36 is moved from its up position to the down position overlying stationary plate 26. Applying force F, which has been observed to be in the range of two to six pounds, while reciprocating and translating slide 34 along direction A cause the stent-catheter assembly to roll along direction R. As the rolling action continues, force F slowly reduces the diameter of stent 10 thus crimping it on to balloon 14 of catheter 11.

Figure 3A:
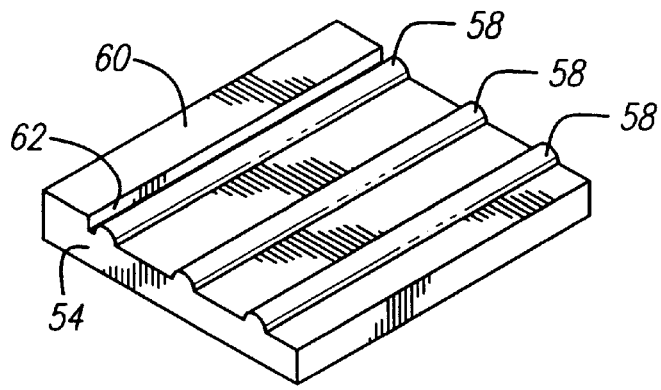
FIGS. 3A and 3B are perspective views showing alternative embodiments of a pad having ridges and a pad having channels that are helpful in gripping the stent.
Figure 3B:
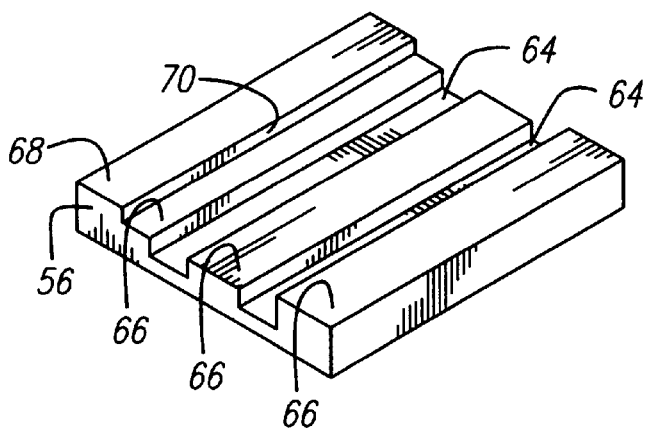

FIGS. 3A and 3B provide perspective views of alternative embodiment pads 54, 56. In pad 54 of FIG. 3A, there are three ridges 58 corresponding to specific cylindrical elements 12 of stent 10. As mentioned earlier, these ridges or contours provide grip points on the stent that improve stability during the crimping process.

A stop or riser 60 having vertical surface 62 against which the distal end of stent 10 abuts helps with alignment of stent 10 within tool 22. Assuming pad 54 is substituted on closing plate 36 or stationary plate 26 in place of pads 40, 42, pad 54 is oriented such that ridges 58 are parallel to ridge 48 as shown in FIG. 2. When the stent-catheter assembly is positioned on pad 54, the distal end of stent 10 abuts vertical surface 62 thus aligning stent 10 lengthwise within the force transmitting surface area of pad 54. Riser 60 thus acts as a stop for stent 10. The height of riser 60 is low enough to clear catheter 11 and guide wire 18 yet still abut stent 10.

Likewise, in the alternative embodiment shown in FIG. 3B, pad 56 includes channels 64 that create raised areas 66 intended to engage corresponding cylindrical elements 12 of stent 10. Pad 56 also includes optional riser 68 having vertical surface 70.

Needless to say, the profiles of ridges 58 or channels 64 can have various shapes and dimensions. For example, the ridges may be pointed as in a cone, angled as in a saw-tooth, or be rounded. The ridges may also be a collection of round pegs closely bunched to hold the stent. Other conventional geometric shapes are contemplated.

It is preferable that the surface directly in contact with stent 10 during the crimping process be slightly softer than the material used on the stent to allow for yield. Elastomer-type materials with high durometers known in the art can be used for the pads, for example. More precisely, the contoured pads can be made from materials such as Mylar, silicone, rubber, or polycarbonate. The entire crimping tool or parts thereof can be made from stainless steel, aluminum, Delrin, polycarbonate, or the like.

The present invention tool is preferably sterilized and intended to be used in a cath lab by a trained technician or cardiologist. As will be appreciated by those skilled in the art, the present invention crimping tool is designed both for single use applications in a cath lab by a physician, or for multiple use applications in a sterile environment in a high volume manufacturing facility. In such a manufacturing facility where sterile conditions exist, the present invention stent crimping tool can be used repeatedly to crimp stents onto balloons until the mechanism wears out. Thus, repeated uses of the present invention are contemplated for controlled, sterile environments, as are single use applications when operated by cath lab personnel.

Furthermore, the present invention crimping tool can be used with any stent that is released without a delivery system. The crimping tool may also be sold alone, because its design is robust enough to undergo many uses.

Other modifications can be made to the present invention without departing from the scope thereof. The specific dimensions, procedural steps, and materials of construction are provided as examples, and substitutes are readily contemplated which do not depart from the invention.

What is claimed is:

1. A stent crimping tool for crimping a stent on to a balloon catheter, comprising:
   a stationary plate;
   a sliding platform, connected to the stationary plate and slidable linearly relative thereto;
   a closing plate hinged to the sliding platform so that the closing plate at least partially overlies the stationary plate in a down position, and swings away from the stationary plate to an up position;
   whereby the stent having been loaded on to the balloon catheter is placed on the stationary plate from a lateral position, and the closing plate is moved to the down position to hold the stent between the closing plate and the stationary plate, so that an external force on the closing plate and translational motion of the closing plate crimp the stent on to the balloon catheter.

2. The stent crimping tool of claim 1, wherein the closing plate and the stationary plate having facing surfaces that include pads for gripping the stent.

3. The stent crimping tool of claim 1, wherein stationary plate includes at least one spacer to control a gap between the stationary plate and the closing plate in the down position.

4. The stent crimping tool of claim 1, wherein the closing plate and the stationary plate having facing surfaces that include opposed contoured pads.

5. The stent crimping tool of claim 4, wherein the contoured pads include longitudinally oriented ridges.

6. The stent crimping tool of claim 4, wherein at least one contoured pad includes a material selected from the group consisting of polyethylene terephthalate, silicone, rubber, or polycarbonate.

7. The stent crimping tool of claim 1, wherein the tool includes a material selected from the group consisting of stainless steel, aluminum, acetal, or polycarbonate.

8. A stent crimping tool for crimping a stent on to a balloon catheter, comprising:
   a base plate having opposed first and second ends;
   a stationary plate disposed on the first end of the base plate;
   a platform disposed on the second end of the base plate, wherein the platform includes a channel;
   a slide having a dove tail formation to slidably engage the channel of the platform to enable translation toward and away from the stationary plate;
   a closing plate hinged to the slide and having a down position at least partially overlying the stationary plate, and swinging away from the stationary plate to an up position; and
   whereby the stent having been loaded on to the balloon catheter is placed on the stationary plate from a lateral position, and the closing plate is moved to the down position to hold the stent between the closing plate and the stationary plate so that an external force on the closing plate and translational motion of the closing plate crimps the stent on to the balloon catheter.

9. The stent crimping tool of claim 8, wherein the closing plate and stationary plate have facing surfaces each including a pad having a ridge.

10. The stent crimping tool of claim 8, wherein the closing plate and stationary plate have facing surfaces each including a pad having a channel.

11. The stent crimping tool of claim 8, wherein the stationary plate includes a pad having at least two ridges aligned with a proximal ring and a distal ring of the stent.

12. The stent crimping tool of claim 8, wherein the tool includes a mandrel disposed inside the balloon catheter.

13. The stent crimping tool of claim 8, wherein the tool includes a spring interconnecting the closing plate to the slide.

14. The stent crimping tool of claim 8, wherein the stationary plate includes at least one spacer disposed on a surface facing the closing plate in the down position.

15. A method for crimping a stent that is preloaded on to a balloon catheter, the method comprising the steps of:

providing a stationary plate;

providing a sliding platform connected to the stationary plate and slidable linearly relative thereto;

providing a closing plate hinged to the sliding platform so that the closing plate at least partially overlies the stationary plate in a down position, and swings away from the stationary plate to an up position;

placing the preloaded stent and balloon catheter on the stationary plate from a lateral position;

moving the closing plate to the down position to hold the preloaded stent and balloon catheter between the closing plate and the stationary plate;

applying an external force on the closing plate to bias the closing plate toward the stationary plate; and applying a translational motion to the closing plate thereby crimping the stent onto the balloon catheter.

16. The method for crimping a stent on to a balloon catheter of claim 15, wherein the stationary plate includes a ridge and the stent includes a ring, and the method further comprises a step of aligning the ring of the stent with the ridge of the stationary plate thereby crimping the stent onto the balloon catheter.

17. The method for crimping a stent on to a balloon catheter of claim 15, wherein the method includes a step of providing a spacer on the stationary plate to set a gap between the stationary plate and the closing plate in the down position.

18. The method for crimping a stent on to a balloon catheter of claim 15, wherein the external force is between 2 to 6 lbf. inclusive.

19. The method for crimping a stent on to a balloon catheter of claim 15, wherein the step of moving the closing plate to the down position further comprises rotating the closing plate about a hinged axis located on the sliding platform.

20. The method for crimping a stent on to a balloon catheter of claim 15, wherein the method further comprises a step of rotating the preloaded stent and balloon catheter.

* * * * *

UNITED STATES PATENT AND TRADEMARK OFFICE
CERTIFICATE OF CORRECTION

PATENT NO. : 6,092,273
DATED : Jul. 25, 2000
INVENTOR(S) : Plaridel K. Villareal It is certified that error appears in the above-identified patent and that said Letters Patent is hereby corrected as shown below:

Title page, under "OTHER PUBLICATIONS", add --<u>The eXTraordinary Stent</u>, C.R. Bard Brochure (undated)--.

Signed and Sealed this

Seventeenth Day of April, 2001

Attest:

NICHOLAS P. GODICI

Attesting Officer     Acting Director of the United States Patent and Trademark Office